US012767639B2

(12) United States Patent
Esumi et al.

(10) Patent No.: US 12,767,639 B2
(45) Date of Patent: Oct. 20, 2026

(54) METHOD FOR PRODUCING HALOVINYL IMIDAZOLE COMPOUND

(71) Applicant: Nippon Soda Co., Ltd., Tokyo (JP)

(72) Inventors: Naoto Esumi, Takaoka (JP); Daiki Tadakuma, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 374 days.

(21) Appl. No.: 18/693,471

(22) PCT Filed: Nov. 16, 2022

(86) PCT No.: PCT/JP2022/042473

§ 371 (c)(1),
(2) Date: Mar. 19, 2024

(87) PCT Pub. No.: WO2023/090336

PCT Pub. Date: May 25, 2023

(65) Prior Publication Data

US 2024/0391879 A1 Nov. 28, 2024

(30) Foreign Application Priority Data

Nov. 19, 2021 (JP) ................................ 2021-188984

(51) Int. Cl.
*C07D 233/64* (2006.01)

(52) U.S. Cl.
CPC ................................ *C07D 233/64* (2013.01)

(58) Field of Classification Search
None
See application file for complete search history.

(56) References Cited

U.S. PATENT DOCUMENTS

| | | | |
|---|---|---|---|
| 4,410,706 | A | 10/1983 | Rothenberg et al. |
| 4,886,891 | A | 12/1989 | Torii et al. |
| 2018/0362470 | A1 | 12/2018 | Hamamoto et al. |
| 2019/0185459 | A1 | 6/2019 | Sakanishi et al. |
| 2020/0010445 | A1 | 1/2020 | Kimura et al. |
| 2021/0269415 | A1 | 9/2021 | Sakanishi et al. |
| 2021/0380554 | A1 | 12/2021 | Sakanishi et al. |
| 2021/0380556 | A1 | 12/2021 | Sakanishi et al. |
| 2022/0002342 | A1 | 1/2022 | MacMillan |

FOREIGN PATENT DOCUMENTS

| | | | |
|---|---|---|---|
| CA | 3115968 | A1 | 5/2020 |
| CN | 101100454 | A | 1/2008 |
| CN | 103420783 | A * | 12/2013 |
| CN | 106866515 | A | 6/2017 |
| EP | 0 187 674 | A2 | 7/1986 |
| EP | 3252046 | A1 | 12/2017 |
| EP | 3372588 | A1 | 9/2018 |
| JP | 58-210067 | A | 12/1983 |
| JP | 61-161225 | A | 7/1986 |
| JP | 63-264429 | A | 11/1988 |
| JP | 04-021672 | A | 1/1992 |
| JP | 2000-178247 | A | 6/2000 |
| JP | 2011-121913 | A | 6/2011 |
| JP | 2017-066077 | A | 4/2017 |
| JP | 2019-019068 | A | 2/2019 |
| JP | 2019-065018 | A | 4/2019 |
| JP | 2022-038431 | A | 3/2022 |

(Continued)

OTHER PUBLICATIONS

Notice of Allowance dated May 21, 2026 in U.S. Appl. No. 18/696,186.

Huang H, Cai J, Tang L, Wang Z, Li F, Deng GJ. “Metal-Free Assembly of Polysubstituted Pyridines from Oximes and Acroleins”, J Org Chem. Feb. 1, 20169; 81(4): 1499-505. doi: 10.1021/acs.joc.5b02624. Epub Jan. 28, 2016. PMID: 26788938. Jan. 28, 2016 (cited in an Office Action dated Jan. 15, 2026 in India App. No. 202447022078).

Ye Wei, Naohiko Yoshikai; “Modular Pyridine Synthesis from Oximes and Enals through Synergistic Copper/Iminium Catalysis”; J. Am. Chem. Soc. 2013, 135, 10, 3756-3759; https://doi.org/10.1021/ja312346s; Feb. 26, 2013 (Feb. 26, 2013) (cited in an Office Action dated Jan. 15, 2026 in India App. No. 202447022078).

Office Action dated Jan. 15, 2026 in India App. No. 202447022078.

Database Registry [Online] Chemical Abstract Service, Columbus, Ohio, US; Nov. 9, 2011 (Nov. 9, 2011), XP093315452, Database accession No. 1343121-58-3, 1341679-36-4, 1339522-22-3 (cited in a Search dated Oct. 14, 2025 in EP App. No. 22895618.1).

(Continued)

*Primary Examiner* — Clinton A Brooks
*Assistant Examiner* — Nicola Maria Bauer
(74) *Attorney, Agent, or Firm* — FITCH, EVEN, TABIN & FLANNERY, LLP

(57) ABSTRACT

The present invention provides a method for producing a compound represented by formula (2) (in the formula, $R^1$ and Q each represent the same as those in formula (1)), the method comprising causing a chemical reaction between sodium hyposulphite and a compound represented by formula (1) (in the formula, $R^1$ represents a C1-6 alkyl group, Q represents a hydrogen atom or a substituted or unsubstituted pyridyl group, X represents a halogeno group, and $R^a$ represents a C1-6 alkyl group) in the presence of a base.

[Chemical formula 1]

(1)

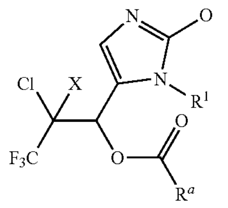

(2)

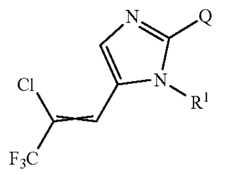

3 Claims, No Drawings

(56) References Cited

FOREIGN PATENT DOCUMENTS

| | | | | | |
|---|---|---|---|---|---|
| TW | 201726628 | A | | 8/2017 | |
| TW | 202024054 | A | | 7/2020 | |
| WO | WO-2005/090333 | A1 | | 9/2005 | |
| WO | 2009/054742 | A2 | | 4/2009 | |
| WO | WO-2017/016910 | A1 | | 2/2017 | |
| WO | WO-2017/050685 | A1 | | 3/2017 | |
| WO | WO-2017104741 | A1 | * | 6/2017 | ................ C07F 7/10 |
| WO | 2018/052035 | A1 | | 3/2018 | |
| WO | WO-2018/194077 | A1 | | 10/2018 | |
| WO | WO-2020/050212 | A1 | | 3/2020 | |
| WO | WO-2020/071304 | A1 | | 4/2020 | |
| WO | WO-2020090585 | A1 | * | 5/2020 | ........... C07D 401/04 |
| WO | WO-2023090345 | A1 | * | 5/2023 | ........... C07D 233/64 |

OTHER PUBLICATIONS

Yoshida Y et al: "TiCl"4/Bu"3N/(catalytic TMSOTf): Efficient Agent for Direct Aldol Addition and Claisen Condensation", Tetrahedron Letters, Elsevier, Amsterdam, NL, vol. 38, No. 0, Dec. 15, 1997 (Dec. 15, 1997), pp. 8727-8730, XP004097162, ISSN: 0040-4039, DOI: 10.1016/S0040-4039(97)10320-3 (cited in a Search dated Oct. 16, 2025 in EP App. 22895626.4).
Search report dated Oct. 14, 2025 in EP App. No. 22895618.1.
Search report dated Oct. 16, 2025 in EP App. No. 22895626.4.
International Search Report dated Feb. 7, 2023 in PCT/JP2022/042473.
International Search Report dated Jan. 24, 2023 in PCT/JP2022/042474.
International Search Report dated Jan. 24, 2023 in PCT/JP2022/042495.
International Search Report dated Jan. 31, 2023 in PCT/JP2022/042500.
Marcoux et al., "A General Preparation of Pyridines and Pyridones via the Annulation of Ketones and Esters," J. Org. Chem., 2001, 66:4194-4199.
Takagi et al., "Synthesis of Fluorine Compounds Using Zing Complex of Halothane," Tetrahedron, 1996, 52(39):12667-12676.
Wikipedia: "Wikipedia", "Sodium dithionite", Jan. 1, 1997 (Jan. 1, 1997), XP093314749, Retrieved from the Internet: URL:https://en.wikipedia.org/wiki/Sodium_dithionite.
Search Report dated Oct. 15, 2025 in EP App. No. 22895617.3.
Office Action dated Jan. 19, 2026 in TW App. No. 111143657 with translation of search report.
Office Action dated Jan. 21, 2026 in TW App. No. 111143659 with translation of search report.
Hilf, J. A., et al., Route to highly substituted pyridines, The Journal of Organic Chemistry, Aug. 31, 2016, vol. 81, No. 21, p. 10376-10382 (cited in a Notice of Allowance dated Apr. 7, 2026 in JP App. No. 2023-562366).
Office Action dated Apr. 7, 2026 in JP App. No. 2023-562359.
Notice of Allowance dated Apr. 7, 2026 in JP App. No. 2023-562366.
Hashimoto et al., (2006), "Practical method for the synthesis of (R)-homopipecolinic acid and (R)-homoproline esters from w-chloroalkanoic acids and available chiral amines," Tetrahedron, 62, pp. 2214-2223. (Year: 2006).
O'Brien et al., (2014), "Radical C-H Functionalization of Heteroarenes under Electrochemical Control," Angewandte Chemie International Edition, 53(44), p. 11868-11871. (Year: 2014).
Huang et al., (2019), "Electricity-driven asymmetric Lewis acid catalysis," Nature Catalysis, 2, p. 34-40 (Year: 2019).
Quayle Action dated Jun. 30, 2026 in U.S. Appl. No. 18/694,784.

* cited by examiner

METHOD FOR PRODUCING HALOVINYL IMIDAZOLE COMPOUND

TECHNICAL FIELD

The present invention relates to a method of producing a halovinyl imidazole compound.

Priority is claimed on Japanese Patent Application No. 2021-188984, filed Nov. 19, 2021, the content of which is incorporated herein by reference.

BACKGROUND ART

Nitrogen-containing heterocycles are main partial structures (building blocks) that constitute compounds that serve as raw materials of pharmaceuticals or agricultural chemicals. In recent years, the development of harmful arthropod control agents having an imidazole ring, a pyridine ring or the like has been actively carried out. For example, Patent Document 1 discloses a compound of formula (A).

[Chemical formula 1]

(A)

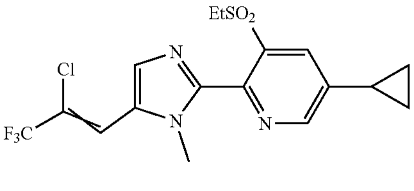

Vinylimidazole compounds are also useful as monomers to produce polymers. For example, Patent Document 2 discloses a method characterized by dehydrogenating a compound selected from the group consisting of 2-alkylimidazoles and 2-alkylimidazolines in the presence of a dehydrogenation catalyst to produce 2-alkenylimidazoles.

Patent Document 3 discloses a method of producing a 1-vinylimidazole derivative, characterized in that a 2-hydroxyethylimidazole derivative is dehydrated in a liquid phase in the presence of an alkali metal hydroxide or alcoholate.

Patent Document 4 discloses a method of producing a vinylimidazole compound, in which a hydroxyethyl group-containing imidazole compound is subjected to a dehydration reaction in the presence of a dehydrating agent in a solvent having a boiling point at normal pressure higher than the boiling point of the vinylimidazole compound at normal pressure by 30° C. or more.

CITATION LIST

Patent Document

[Patent Document 1]
WO 2020/090585 A
[Patent Document 2]
Japanese Unexamined Patent Application Publication No. Sho 58-210067
[Patent Document 3]
Japanese Unexamined Patent Application Publication No. Hei 4-21672
[Patent Document 4]
Japanese Unexamined Patent Application Publication No. 2011-121913

SUMMARY OF INVENTION

Technical Problem

An object of the present invention is to provide a method of producing a halovinyl imidazole compound, which is one of building blocks.

Solution to Problem

The present invention including the following aspects was completed as a result of repeated studies to achieve the above-mentioned objects.

(1) A method of producing a compound of formula (2) (hereinafter, may be referred to as compound (2)), including: chemically reacting a compound of formula (1) (hereinafter, may be referred to as compound (1)) and sodium hyposulfite in the presence of a base,

[Chemical formula 2]

(1)

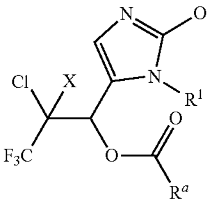

(in the formula (1), $R^1$ is a C1-6 alkyl group, Q is a hydrogen atom, or a substituted or unsubstituted pyridyl group, X is a halogeno group, and $R^a$ is a C1-6 alkyl group).

[Chemical formula 3]

(2)

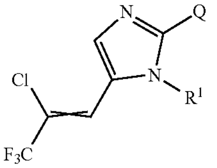

(in the formula (2), $R^1$ and Q are identical to $R^1$ and Q in the formula (1), respectively).

(2) The production method according to (1) mentioned above, further including: obtaining the compound of formula (1) by a method including: chemically reacting a compound of formula (3) (hereinafter, may be referred to as compound (3)) and a compound of formula (4) (hereinafter, may be referred to as compound (4)) in the presence of a base or a metal alkoxide; and chemically reacting the reaction product of the above-mentioned chemical reaction and a compound of formula (5) (hereinafter, may be referred to as compound (5)).

[Chemical formula 4]

(3)

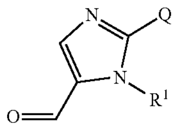

(In the formula (3), $R^1$ is a C1-6 alkyl group, and Q is a hydrogen atom, or a substituted or unsubstituted pyridyl group).

[Chemical formula 5]

(4)

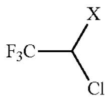

(In the formula (4), X is a halogeno group).

[Chemical formula 6]

(5)

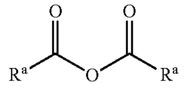

(In the formula (5), $R^a$ is a C1-6 alkyl group).

(3) A compound of formula (2a1), formula (2a2), or formula (2a3).

[Chemical formula 7]

(2a1)

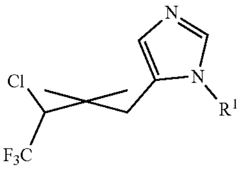

(2a2)

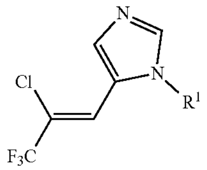

(2a3)

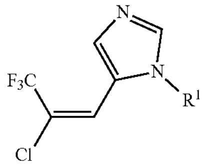

(In the formula (2a1), formula (2a2), or formula (2a3), $R^1$ is a C1-6 alkyl group).

Advantageous Effects of Invention

According to the production method of the present invention, the compound of formula (2) can be obtained in a high yield.

DESCRIPTION OF EMBODIMENTS

In the present invention, the term "unsubstituted" refers to a group consisting of a mother nucleus. In the case where only the name of a group serving as a mother nucleus is provided without accompanying the term "substituted", this refers to "unsubstituted" unless specifically indicated otherwise.

On the other hand, the term "substituted" means that any hydrogen atom of a group serving as a mother nucleus is substituted with a group (substituent) having a structure that is identical to or different from the mother nucleus. Thus, a "substituent" is another group bound to a group serving as the mother nucleus. The number of substituents may be one or two or more. Two or more substituents may be identical to or different from each other.

The term "C1-6", for example, indicates that the number of carbon atoms of the group serving as the mother nucleus is 1 to 6. The number of carbon atoms does not include the number of carbon atoms present in substituents. For example, a butyl group having an ethoxy group as a substituent thereof is classified as a C2 alkoxy C4 alkyl group.

There are no particular limitations on "substituents" provided that they are 10 chemically allowed and achieve effects of the present invention.

Examples of groups that can serve as "substituents" include the following groups:

C1-6 alkyl groups such as a methyl group, an ethyl group, a n-propyl group, an i-propyl group, a n-butyl group, a s-butyl group, an i-butyl group, a t-butyl group, a n-pentyl group, and a n-hexyl group;

C2-6 alkenyl groups such as a vinyl group, a 1-propenyl group, a 2-propenyl group (an allyl group), a 1-butenyl group, a 2-butenyl group, a 3-butenyl group, a 1-methyl-2-propenyl group, and a 2-methyl-2-propenyl group;

C2-6 alkynyl groups such as an ethynyl group, a 1-propynyl group, a 2-propynyl group, a 1-butynyl group, a 2-butynyl group, a 3-butynyl group, and a 1-methyl-2-propynyl group;

C3-6 cycloalkyl groups such as a cyclopropyl group, a cyclobutyl group, a cyclopentyl group, and a cyclohexyl group;

a phenyl group;

three- to six-membered heterocyclyl groups;

C1-6 alkoxy groups such as a methoxy group, an ethoxy group, a n-propoxy group, an i-propoxy group, a n-butoxy group, a s-butoxy group, an i-butoxy group, and a t-butoxy group;

C6-10 aryloxy groups such as a phenoxy group, and a naphthoxy group;

five- or six-membered heteroaryloxy groups such as a thiazolyloxy group, and a pyridyloxy group;

C1-6 alkoxycarbonyl groups such as a methoxycarbonyl group, an ethoxycarbonyl group, a n-propoxycarbonyl group, an i-propoxycarbonyl group, a n-butoxycarbonyl group, and a t-butoxycarbonyl group;

halogeno groups such as a fluoro group, a chloro group, a bromo group, and an iodo group;

C1-6 haloalkyl groups such as a chloromethyl group, a chloroethyl group, a trifluoromethyl group, a 1,2-dichloro-n-propyl group, a 1-fluoro-n-butyl group, and a perfluoro-n-pentyl group;

C1-6 haloalkoxy groups such as a trifluoromethoxy group, a 2-chloro-n-propoxy group, and a 2,3-dichlorobutoxy group;

a formylamino group;

C1-6 alkylcarbonylamino groups such as an acetylamino group, a propanoylamino group, a butyrylamino group, and an i-propylcarbonylamino group;

C1-6 alkoxycarbonylamino groups such as a methoxycarbonylamino group, an ethoxycarbonylamino group, a n-propoxycarbonylamino group, and an i-propoxycarbonylamino group;

unsubstituted or substituted aminocarbonyl groups such as an aminocarbonyl group, a dimethylaminocarbonyl group, a phenylaminocarbonyl group, and a N-phenyl-N-methylaminocarbonyl group;

C1-6 alkylthio groups such as a methylthio group, an ethylthio group, a n-propylthio group, an i-propylthio group, a n-butylthio group, an i-butylthio group, a s-butylthio group, and a t-butylthio group;

C1-6 haloalkylthio groups such as a trifluoromethylthio group, and a 2,2,2-trifluoroethylthio group;

C1-6 alkylsulfonyl groups such as a methylsulfonyl group, an ethylsulfonyl group, and a t-butylsulfonyl group;

C1-6 haloalkylsulfonyl groups such as a trifluoromethylsulfonyl group, and a 2,2,2-trifluoroethylsulfonyl group;

a cyano group; and a nitro group.

Any hydrogen atom of the "substituent" may be substituted with a group having a different structure. Examples of such a substituent include C1-6 alkyl groups, C1-6 haloalkyl groups, C1-6 alkoxy groups, C1-6 haloalkoxy groups, halogeno groups, a cyano group, and a nitro group.

The "three- to six-membered heterocyclyl group" is one which contains, as a ring member atom, one to four hetero atoms selected from the group consisting of a nitrogen atom, an oxygen atom and a sulfur atom. The heterocyclyl group may be monocyclic or polycyclic. If at least one ring of a polycyclic heterocyclyl group is a hetero ring, the remaining rings thereof may be any of saturated alicyclic rings, unsaturated alicyclic rings and aromatic rings. Examples of the "three- to six-membered heterocyclyl group" include three- to six-membered saturated heterocyclyl groups, five- or six-membered heteroaryl groups, and five- or six-membered partially unsaturated heterocyclyl groups.

Examples of the three- to six-membered saturated heterocyclyl groups include an aziridinyl group, an epoxy group, a pyrrolidinyl group, a tetrahydrofuranyl group, a thiazolidinyl group, a piperidyl group, a piperazinyl group, a morpholinyl group, a dioxolanyl group, and a dioxanyl group.

Examples of the five-membered heteroaryl groups include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group.

Examples of the six-membered heteroaryl groups include a pyridyl group, a pyrazinyl group, a pyrimidinyl group, a pyridazinyl group, and a triazinyl group.

Examples of the five-membered partially-unsaturated heterocyclyl groups include a pyrrolinyl group, a dihydrofuranyl group, an imidazolinyl group, a pyrazolinyl group, an oxazolinyl group, and an isooxazolinyl group.

Examples of the six-membered partially-unsaturated heterocyclyl groups include a dihydropyranyl group.

A method of producing a compound (2) of the present invention includes chemically reacting a compound (1) and a sodium hyposulfite in the presence of a base (hereinafter, may be referred to as a third reaction).

The compound (1) is represented by the following formula (1).

[Chemical formula 8]

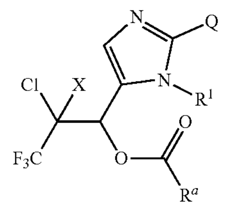

(1)

In the formula (1), $R^1$ is a C1-6 alkyl group.

The C1-6 alkyl group as $R^1$ may be linear or branched. Examples of the C1-6 alkyl group as $R^1$ include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, a 2,2-dimethylpropyl group, and an i-hexyl group, In the formula (1), Q is a hydrogen atom, or a substituted or unsubstituted pyridyl group. Q is preferably a hydrogen atom.

Examples of a substituent on the "pyridyl group" as Q include: halogeno groups such a fluoro group, a chloro group, a bromo group, and an iodo group; C1-6 alkyl groups such as a methyl group, an ethyl group, a n-propyl group, an i-propyl group, a n-butyl group, a s-butyl group, an i-butyl group, a t-butyl group, a n-pentyl group, and a n-hexyl group; C1-6 haloalkyl groups such as a difluoromethyl group, a trifluoromethyl group, a perfluoroethyl group, a 1,2,2,3,3,3-hexafluoropropyl group, a perfluoropropyl group, and a 1,2,3,3,3-pentafluoro-2-(trifluoromethyl) propyl group; C3-6 cycloalkyl groups such as a cyclopropyl group, and a cyclobutyl group; C1-6 alkoxy groups such as a methoxy group, an ethoxy group, a n-propoxy group, an i-propoxy group, a n-butoxy group, a s-butoxy group, an i-butoxy group, and a t-butoxy group; C1-6 haloalkoxy groups such as a difluoromethoxy group, a trifluoromethoxy group, a 2,2-difluoroethyl group, and 2,2,2-trifluoroethyl group; C1-6 alkylthio groups such as a methylthio group, and an ethylthio group; C1-6 alkylsulfinyl groups such as a methylsulfinyl group, and an ethylsulfinyl group; C1-6 alkylsulfonyl groups such as a methylsulfonyl group and an ethylsulfonyl group; a phenyl group; phenyl groups substituted with a halogeno group, a C1-6 alkyl group, a C1-6 haloalkyl group, or a C1-6 haloalkoxy group; five- or six-membered heteroaryl groups such as a triazolyl group, and a pyrimidinyl group; five- or six-membered heteroaryl groups substituted with a halogeno group, a C1-6 alkyl group, a C1-6 haloalkyl group, or a C1-6 haloalkoxy group; and a cyano group.

In the formula (1), X is a halogeno group.

Examples of the "halogeno group" as X include a fluoro group, a chloro group, a bromo group, and an iodo group.

X is preferably a chloro group or a bromo group.

In the formula (1), $R^a$ is a C1-6 alkyl group.

Examples of the "C1-6 alkyl group" as $R^a$ include the same groups as those mentioned as $R^1$.

The compound (1) used in the present invention may be one which is synthesized by oneself using a conventionally-known method, or one which is synthesized by another person by any method and commercially available.

The compound (1) used in the present invention may be obtained by a method including: chemically reacting a compound (3) and a compound (4) in the presence of a base or a metal alkoxide (hereinafter, may be referred to as first reaction); and chemically reacting the reaction product of the first reaction and a compound (5) (hereinafter, may be referred to as second reaction), for example.

[Chemical formula 9]

(3)

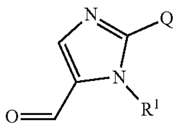

In the formula (3), $R^1$ is a C1-6 alkyl group, and Q is a hydrogen atom, or a substituted or unsubstituted pyridyl group.

Examples of the compound (3) include 1-methyl-1H-imidazole-5-carbaldehyde.

[Chemical formula 10]

(4)

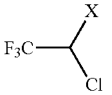

In formula (4), X is a halogeno group.

Examples of the compound (4) include 2,2-dichloro-1,1,1-trifluoroethane (HCFC-123), and 2-bromo-2-chloro-1,1,1-trifluoroethane (halothane), and 2-bromo-2-chloro-1,1,1-trifluoroethane is preferable.

[Chemical formula 11]

(5)

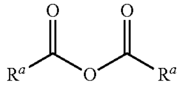

In the formula (5), $R^a$ is a C1-6 alkyl group.

Examples of the compound (5) include acetic anhydride and propionic anhydride.

The compound (3), compound (4) and compound (5) used in the first reaction or the second reaction may be ones which are synthesized by oneself using conventionally-known methods, or ones which are synthesized by another person by any methods and commercially available.

In the first reaction, the amount of the compound (4) relative to one mol of the compound (3) is, for example, 1.0 mol to 5.0 mol, and preferably 1.2 mol to 2.0 mol.

Examples of the base which is made to be present in the first reaction include: inorganic bases such as sodium carbonate, sodium hydrogen carbonate, potassium carbonate, potassium hydrogen carbonate, sodium hydroxide, potassium hydroxide, sodium hydride, and potassium hydride; and organic bases such as triethylamine, tetramethylethylenediamine, N,N-diisopropylamine, N,N-dimethylaniline, N,N-diethylaniline, 4-methylmorpholine, 1-azabicyclo[2.2.2]octane, 1,4-diazabicyclo[2.2.2] octane (abbreviation: DABCO), 1,8-diazabicyclo[5.4.0]undec-7-ene, 1,5-diazabicyclo[4.3.0]non-5-ene, pyridine, 4-(dimethylamino)pyridine and 2,6-dimethylpyridine.

The amount of the base used relative to one mole of the compound (3) is, for example, 1.0 mol to 5.0 mol, and preferably 1.5 mol to 2.0 mol.

Examples of the metal alkoxide which is made to be present in the first reaction include sodium methoxide, sodium ethoxide, and potassium t-butoxide, and potassium t-butoxide is preferably used.

The amount of the metal alkoxide used relative to one mole of the compound (3) is, for example, 1.0 mol to 5.0 mol, and preferably 1.2 mol to 2.0 mol.

The first reaction may be carried out in the absence of any solvents or in a solvent. The first reaction is preferably carried out in an organic solvent in view of operability.

Examples of the organic solvent include: ethers such as diethyl ether, diisopropyl ether, diethylene glycol dimethyl ether (product name: diglyme) and tetrahydrofuran (abbreviation: THF); halogenated hydrocarbons such as dichloromethane, chloroform, and 1,2-dichloroethane (abbreviation: DCE); aliphatic hydrocarbons such as pentane, hexane, cyclohexane, heptane and octane; aromatic hydrocarbons such as toluene and xylene; aprotic polar solvents such as N,N-dimethylformamide (abbreviation: DMF), N,N'-dimethylpropyleneurea (abbreviation: DMPU) hexamethylphosphoric triamide (abbreviation: HMPA); and acetonitrile, and ethers such as tetrahydrofuran are preferably used.

The amount of the organic solvent used relative to one part by weight of the compound (3) is preferably 10 parts by weight to 2000 parts by weight.

The addition order of the compound (3), the compound (4), and a metal alkoxide or a base, used in the first reaction, and an organic solvent used as necessary, to the reaction site is not particularly limited. For example, it is preferable that a solvent be put in a reaction container, and then the compound (3) and the compound (4) be added thereto, followed by adding a metal alkoxide or a base thereto.

The temperature at which mixing is conducted is preferably −70° C. to 0° C., and more preferably −70° C. to −50° C.

When mixing is conducted, mixing is preferably conducted by stirring.

A metal alkoxide or a base is preferably added gradually by conducting dropwise-addition, or the like.

The temperature in the first reaction is preferably −70° C. to 0° C., and more preferably −70° C. to −50° C.

The pressure in the first reaction is not particularly limited, and is, for example, an ordinary pressure.

The reaction time in the first reaction is, for example, five minutes to 24 hours, and more preferably five minutes to one hour.

The first reaction is preferably carried out under an inert gas atmosphere.

After the first reaction is completed, a liquid containing the first reaction product may be used directly in the second reaction. Alternatively, after the first reaction is completed, a liquid containing the first reaction product may be subjected to a post-treatment, and further to a purification, as needed. The post-treatment may be an operation of extraction with an organic solvent, followed by drying or concentrating the resultant organic layer. The purification may be an operation such as recrystallization or chromatography.

In the second reaction, the amount of the compound (5) relative to one mol of the compound (3) is, for example, 1.0 mol to 5.0 mol, and preferably 1.2 mol to 3.0 mol.

The temperature in the second reaction is preferably −70° C. to 0° C., and more preferably −70° C. to −50° C.

The pressure in the second reaction is not particularly limited, and, for example, an ordinary pressure.

The reaction time in the second reaction is, for example, 0.5 hours to 24 hours, and preferably 0.5 hours to 2 hours.

The second reaction is preferably carried out under an inert gas atmosphere.

After the second reaction is completed, a liquid containing the compound (1) may be used directly in the third reaction. Alternatively, after the second reaction is completed, a liquid containing the compound (1) may be subjected to a post-treatment, and further to a purification, as needed. The post-treatment may be an operation of extraction with an organic solvent, followed by drying or concentrating the resultant organic layer. The purification may be an operation such as recrystallization or chromatography.

The sodium hyposulfite can be obtained by electrolytically reducing sodium hydrogen sulfite. Alternatively, the sodium hyposulfite can be obtained by reaction of a sulfur dioxide and a sodium salt mediated by a metal zinc and purification. The sodium hyposulfite has a strong reducing power.

The amount of the sodium hyposulfite used relative to one mol of the compound (1) is, for example, 1.0 mol to 5.0 mol, and is preferably 1.1 mol to 3.0 mol.

Examples of the base which is made to be present in the third reaction include: inorganic bases such as sodium carbonate, sodium hydrogen carbonate, potassium carbonate, potassium hydrogen carbonate, sodium hydroxide, potassium hydroxide, sodium hydride, and potassium hydride; and organic bases such as triethylamine, tetramethylethylenediamine, N,N-diisopropylamine, N,N-dimethylaniline, N,N-diethylaniline, 4-methylmorpholine, 1-azabicyclo[2.2.2]octane, 1,4-diazabicyclo[2.2.2] octane (abbreviation: DABCO), 1,8-diazabicyclo[5.4.0]undec-7-ene, 1,5-diazabicyclo[4.3.0]non-5-ene, pyridine, 4-(dimethylamino)pyridine and 2,6-dimethylpyridine, and inorganic acids such as sodium hydrogen carbonate are preferably used.

The amount of the base used relative to one mol of the compound (1) is, for example, 1.0 mol to 5.0 mol, and is preferably 1.1 mol to 3.0 mol.

The third reaction may be carried out in the absence of any solvents or in a solvent. The reaction is preferably carried out in a solvent in view of operability. Since sodium hyposulfite is used, a mixed solvent of water and an organic solvent is preferably used. Examples of the organic solvent include: alcohols such as methanol and ethanol; ketones such as acetone, and methylethylketone; ethers such as diethyl ether, diisopropyl ether, diethylene glycol dimethyl ether (product name: diglyme) and tetrahydrofuran (abbreviation: THF); aromatic hydrocarbons such as toluene and xylene; aprotic polar solvents such as N,N-dimethylformamide (abbreviation: DMF), N,N'-dimethylpropyleneurea (abbreviation: DMPU), and hexamethylphosphoric triamide (abbreviation: HMPA); and acetonitrile; and ketones such as acetone are preferably used.

The amount of the solvent used relative to one part by weight of the compound (1) is preferably 2 parts by weight to 100 parts by weight.

The addition order of the compound (1), the sodium hyposulfite, and the base, used in the third reaction, and the solvent used as necessary, to the reaction site is not particularly limited.

One embodiment includes: adding the compound (1) to a solvent in a container or in the absence of a solvent; adding sodium hyposulfite and a base thereto to obtain a mixed liquid, and stirring the mixed liquid to terminate the chemical reaction. It is preferable that mixing be conducted by stirring.

All of each substance may be added at once or a small amount thereof may be added gradually and separately.

The temperature in the third reaction is not particularly limited, and is, for example, 0° C. to the boiling point of a solvent, and, for example, approximately 20° C. to 30° C.

The pressure in the third reaction is, for example, 0.1 MPa to 1 MPa, and preferably 0.1 MPa to 0.5 MPa.

The reaction time in the third reaction is not particularly limited, and is, for example, 0.5 hours to 24 hours.

The third reaction is preferably carried out under an inert gas atmosphere.

The third reaction is preferably quenched by adding a saturated aqueous solution of sodium hydrogen carbonate.

After the third reaction is completed, extraction may be conducted with an organic solvent, and the resultant organic layer may be subjected to a post-treatment such as drying or concentrating. Furthermore, if necessary, the resultant in the third reaction may be purified by an operation such as recrystallization or chromatography.

The compound (2) obtained by the production method according to the present invention is represented by formula (2).

[Chemical formula 12]

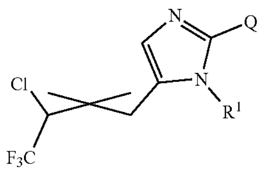

(2)

In the formula (2), $R^1$ and Q are the same as those in the formula (1), respectively.

The following notation in the chemical formula indicates a double bond whose steric configuration is not defined (undefined double stereo bond).

[Chemical formula 13]

Stereoisomers may be separated and purified by an operation such as chromatography.

Among the compounds (2) obtained by the production method according to the present invention, a compound of the following formula (2a1), formula (2a2), or formula (2a3) is a novel compound and is particularly useful as a production intermediate of a pharmaceutical or agricultural chemical or a monomer to produce a polymer.

[Chemical formula 14]

(2a1)

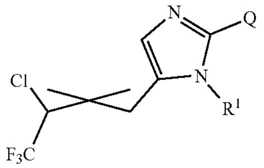

(2a2)

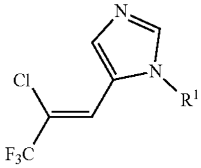

(2a3)

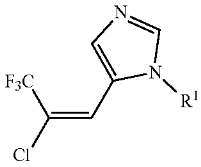

In the formula (2a1), formula (2a2), or formula (2a3), $R^1$ is a C1-6 alkyl group, and is preferably a methyl group.

As the compounds of the formula (2a1), formula (2a2), or formula (2a3), the following compounds are preferable.

[Chemical formula 15]

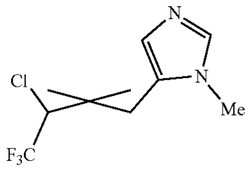

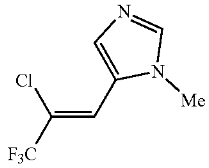

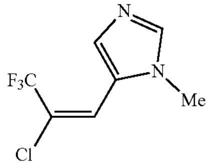

The present invention will be described more specifically below with reference to Examples. In addition, the present invention is not limited to the following examples.

Example 1

(EZ)-5-(2-chloro-3,3,3-trifluoroprop-1-en-1-yl)-1-methyl-1H-imidazole was produced by the following procedure.

Step 1

Synthesis of 2-bromo-2-chloro-3,3,3-trifluoro-1-(1-methyl-1H-imidazol-5-yl) propyl acetate

[Chemical formula 16]

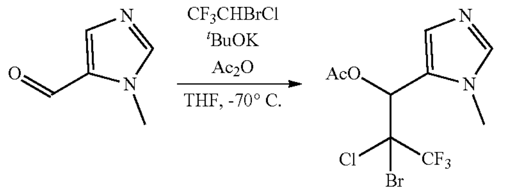

1-Methyl-1H-imidazole-5-carbaldehyde (37 g) and halothane (92.8 g, 1.4 eq.) were dissolved in tetrahydrofuran (1100 mL), and then cooled to −70° C. Potassium t-butoxide (49.0 g, 1.3 eq.) diluted with tetrahydrofuran (700 mL) was added dropwise slowly thereto while conducting stirring, and then stirring was continued for five minutes. Then, acetic acid anhydride (54.8 g, 1.6 eq.) was added thereto, and the mixture was stirred at −70° C. for one hour. Then, the temperature was returned to room temperature. The resultant liquid was quenched by adding a saturated aqueous solution of sodium hydrogen carbonate thereto. Then, the resultant was extracted with ethyl acetate. The obtained organic layer was concentrated under reduced pressure to obtain 107.9 g of a crude product (crude yield 92%).

Step 2

Synthesis of (EZ)-5-(2-chloro-3,3,3-trifluoroprop-1-en-1-yl)-1-methyl-1H-imidazole

[Chemical formula 17]

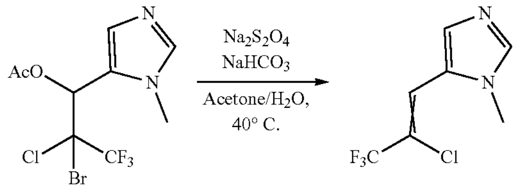

A crude product (2-bromo-2-chloro-3,3,3-trifluoro-1-(1-methyl-1H-imidazol-5-yl) propyl acetate (24.3 g) obtained in the step 1, sodium hyposulfite (24.2 g, 2 eq.), and sodium hydrogen carbonate (11.7 g, 2 eq.) were mixed in acetone (140 mL), and stirred at room temperature. Water (27 mL) was added dropwise thereto while conducting stirring. Then, the temperature was raised to 40° C., and stirring was conducted for two hours. After the temperature was returned to room temperature, a saturated aqueous solution of sodium hydrogen carbonate was added to the resultant, and the mixture was extracted with ethyl acetate. The obtained organic layer was concentrated under reduced pressure, and the resultant concentrate was purified by silica gel chromatography, thereby obtaining 12.8 g of the target product (yield 88%, E/Z=20/80).

NMR signals of the (EZ)-5-(2-chloro-3,3,3-trifluoroprop-1-en-1-yl)-1-methyl-1H-imidazole are shown below.

1H-NMR (400 MHz, $CDCl_3$):

Z isomer δ 7.97 (s, 1H), 7.58 (s, 1H), 7.10 (s, 1H), 3.70 (s, 3H).

E isomer δ 7.52 (s, 1H), 7.37 (s, 1H), 6.86 (s, 1H), 3.65 (s, 3H).

19F-NMR (376 MHz, $CDCl_3$):

Z isomer δ −67.9 (s).

E isomer δ −63.2 (s).

INDUSTRIAL APPLICABILITY

The production method of the present invention makes it possible to efficiently obtain a halovinyl imidazole compound, which is the main partial structure that constitutes a compound which serves as a raw material of a pharmaceutical or agricultural chemical.

The invention claimed is:

1. A method of producing a compound of formula (2), comprising:

chemically reacting a compound of formula (1) and a sodium hyposulfite in a presence of a base,

[Chemical formula 1]

(1)

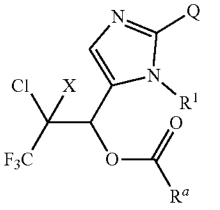

in the formula (1), $R^1$ is a C1-6 alkyl group, Q is a hydrogen atom or a substituted or unsubstituted pyridyl group, X is a halogeno group, and $R^a$ is a C1-6 alkyl group,

[Chemical formula 2]

(2)

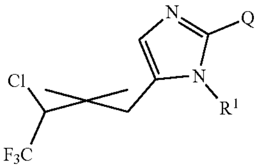

in the formula (2), $R^1$ and Q are identical to $R^1$ and Q in the formula (1), respectively.

2. The production method according to claim 1, further comprising: obtaining the compound of formula (1) by a method comprising:

chemically reacting a compound of formula (3):

[Chemical formula 3]

(3)

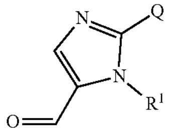

in the formula (3), $R^1$ is a C1-6 alkyl group, and Q is a hydrogen atom or a substituted or unsubstituted pyridyl group, and a compound of formula (4):

[Chemical formula 4]

(4)

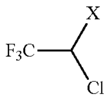

in the formula (4), X is a halogeno group, in a presence of a base or a metal alkoxide; and chemically reacting a reaction product of the chemical reaction and a compound of formula (5):

[Chemical formula 5]

(5)

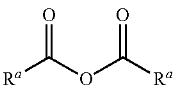

in the formula (5), $R^{1a}$ is a C1-6 alkyl group.

3. A compound of, formula (2a2), or formula (2a3):

(2a2)

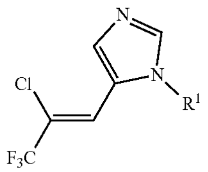

(2a3)

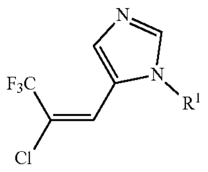

in the, formula (2a2), or formula (2a3), $R^1$ is a C1-6 alkyl group.

* * * * *